US009463116B2

(12) United States Patent
Durrie et al.

(10) Patent No.: US 9,463,116 B2
(45) Date of Patent: *Oct. 11, 2016

(54) LASER CORNEAL FLAP CUTTING SYSTEM AND ASSOCIATED METHODS

(71) Applicant: Alcon RefractiveHorizons, Inc., Fort Worth, TX (US)

(72) Inventors: Daniel S. Durrie, Mission Hills, KS (US); George H. Pettit, Fort Worth, TX (US); John A. Campin, Southlake, TX (US)

(73) Assignee: ALCON REFRACTIVESHORIZONS, INC.

( * ) Notice: Subject to any disclaimer, the term of this patent is extended or adjusted under 35 U.S.C. 154(b) by 0 days.

This patent is subject to a terminal disclaimer.

(21) Appl. No.: 14/575,562

(22) Filed: Dec. 18, 2014

(65) Prior Publication Data

US 2015/0105761 A1  Apr. 16, 2015

Related U.S. Application Data

(63) Continuation of application No. 11/491,636, filed on Jul. 24, 2006, now Pat. No. 8,945,102.

(60) Provisional application No. 60/703,671, filed on Jul. 29, 2005.

(51) Int. Cl.
*A61B 19/00* (2006.01)
*A61B 18/20* (2006.01)
*A61F 9/008* (2006.01)

(52) U.S. Cl.
CPC ........... *A61F 9/00802* (2013.01); *A61F 9/008* (2013.01); *A61F 9/00806* (2013.01);

(Continued)

(58) Field of Classification Search
CPC ............... A61F 9/008; A61F 9/00802; A61F 9/00804; A61F 9/00806; A61F 9/00825; A61F 9/00827; A61F 9/00836; A61F 2009/00844; A61F 2009/00872; A61F 2009/00878; A61F 2009/0088; A61F 2009/00882
USPC .............................. 606/4–6, 10–12; 128/898
See application file for complete search history.

(56) References Cited

U.S. PATENT DOCUMENTS

| 6,210,399 B1 * | 4/2001 | Parel ...................... A61F 9/008 606/10 |
| 6,299,309 B1 | 10/2001 | Ruiz ............................. 351/212 |

(Continued)

OTHER PUBLICATIONS

Touboul D, Salin F, Mortemousque B, Chabassier P, Mottay E, Léger F, Colin J., Advantages and disadvantages of the femtosecond laser microkeratome,J Fr Ophtalmol. May 2005;28(5):535-46.

*Primary Examiner* — Ahmed Farah

(57) ABSTRACT

A method for performing wavefront-guided laser surgery on a cornea includes the step of calculating a corneal flap configuration based upon collected anatomical information on an eye and wavefront data on a cornea of the eye. Such data may be collected by, for example, an aberrometer, although this is not intended as a limitation. The calculated configuration is transmitted to a processor in controlling relation to a corneal flap-cutting device. The flap-cutting device is used to create a corneal flap based upon the calculated configuration. A system for performing wavefront-guided laser surgery on a cornea includes a processor for receiving the anatomical information and wavefront data. A software package is adapted to calculate the corneal flap configuration and to control a conical flap-cutting device to cut a corneal flap commensurate with the calculated corneal flap configuration.

6 Claims, 2 Drawing Sheets

(52) U.S. Cl.
CPC .... *A61F9/00836* (2013.01); *A61F 2009/0088* (2013.01); *A61F 2009/00846* (2013.01); *A61F 2009/00872* (2013.01)

(56) References Cited

U.S. PATENT DOCUMENTS

| | | | |
|---|---|---|---|
| 6,755,819 B1* | 6/2004 | Waelti | A61F 9/00804 606/4 |
| 6,908,196 B2 | 6/2005 | Herekar et al. | 351/221 |
| 7,226,443 B1 | 6/2007 | Campin et al. | 606/5 |
| 7,237,898 B1 | 7/2007 | Hohla et al. | 351/246 |
| 8,945,102 B2* | 2/2015 | Durrie | A61F 9/008 128/898 |
| 2002/0052615 A1 | 5/2002 | Ross et al. | 606/166 |
| 2002/0082629 A1 | 6/2002 | Cox et al. | 606/166 |
| 2002/0111607 A1 | 8/2002 | Bille | 606/5 |
| 2003/0100893 A1 | 5/2003 | Bille | 606/4 |
| 2003/0208190 A1 | 11/2003 | Roberts et al. | 606/5 |
| 2004/0054358 A1* | 3/2004 | Cox | A61F 9/00806 606/5 |
| 2004/0116910 A1* | 6/2004 | Markman | A61B 3/1005 606/5 |
| 2005/0096640 A1 | 5/2005 | Dai et al. | 606/10 |
| 2005/0187540 A1 | 8/2005 | Mrochen et al. | 606/5 |
| 2006/0173445 A1* | 8/2006 | Bille | A61B 3/1015 606/5 |
| 2007/0161972 A1* | 7/2007 | Felberg | A61F 9/00806 606/4 |
| 2011/0224657 A1* | 9/2011 | Stevens | A61F 9/008 606/5 |

* cited by examiner

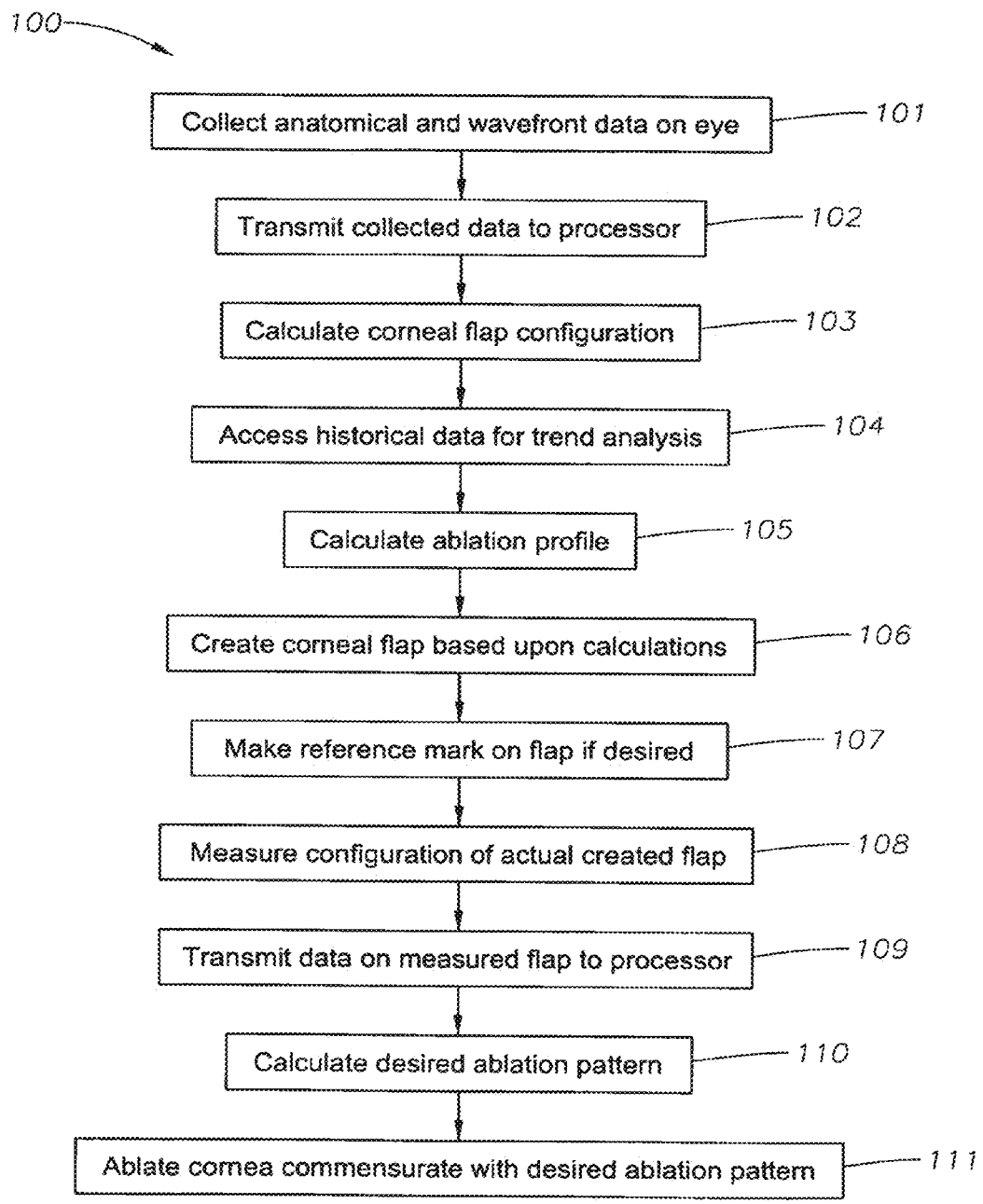

LASER CORNEAL FLAP CUTTING SYSTEM AND ASSOCIATED METHODS

CROSS REFERENCE TO RELATED APPLICATIONS

The present application is a continuation of U.S. application Ser. No. 11/491,636, filed Jul. 24, 2006, titled "LASER CORNEAL FLAP CUTTING SYSTEM AND ASSOCIATED METHODS," (now allowed), which claims the benefit of U.S. provisional application Ser. No. 60/703,671, filed Jul. 29, 2005, titled "LASER CORNEAL FLAP CUTTING SYSTEM AND ASSOCIATED METHODS," the disclosures of which are incorporated by reference in their entirety.

TECHNICAL FIELD OF THE INVENTION

The present invention relates to systems and methods for performing laser-assisted corneal surgery, and, more particularly, to such systems and methods for integrating the cutting of a corneal flap with wavefront-guided refractive laser surgery.

BACKGROUND OF THE INVENTION

It is known in the art to perform corneal ablation by means of wavefront-guided refractive laser surgery. Typically a wavefront sensor measures an aberration map and its position relative to anatomical landmarks, which can be intrinsic or externally applied features. Aberration data, sometimes along with geometric registration information, can be transferred directly to a treatment excimer laser.

It is also known to use a femtosecond laser to cut a corneal flap prior to performing the corneal ablation. However, these procedures are not known to be coordinated, nor is a system known for optimizing the flap-cutting procedure within the limits of a flap-cutting device.

Therefore, it would be advantageous to provide a system and method for coordinating corneal ablation with the flap-cutting procedure and for optimizing same.

BRIEF SUMMARY OF THE INVENTION

The present invention is directed to a system and method for performing wavefront-guided laser surgery on a cornea. The method comprises the step of calculating a corneal flap configuration based upon collected anatomical information on an eye and wavefront data on a cornea of the eye. Such data may be collected by, for example, an aberrometer, although this is not intended as a limitation.

The calculated configuration is transmitted to a processor in controlling relation to a corneal flap-cutting device. The flap-cutting device is used to create a corneal flap based upon the calculated configuration.

A system for performing wavefront-guided laser surgery on a cornea comprises a processor and means for transmitting to the processor anatomical information collected on an eye and wavefront data collected on a cornea of the eye.

A software package is installable on the processor that is adapted to calculate a corneal flap configuration based upon the anatomical information and wavefront data. The corneal flap configuration can be an optimal flap configuration within the limits of the software package, the processor and the anatomical information and wavefront data provided to the processor, as well as based on any other predefined limits imposed by the software for a given application. The software package is also adapted to control a corneal flap-cutting device to cut a corneal flap commensurate with the calculated optimal corneal flap configuration.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings in which like reference numbers indicate like features and wherein:

FIG. 2 is a flowchart of an exemplary laser surgery method of the present invention.

DETAILED DESCRIPTION OF THE INVENTION

Figure 1:
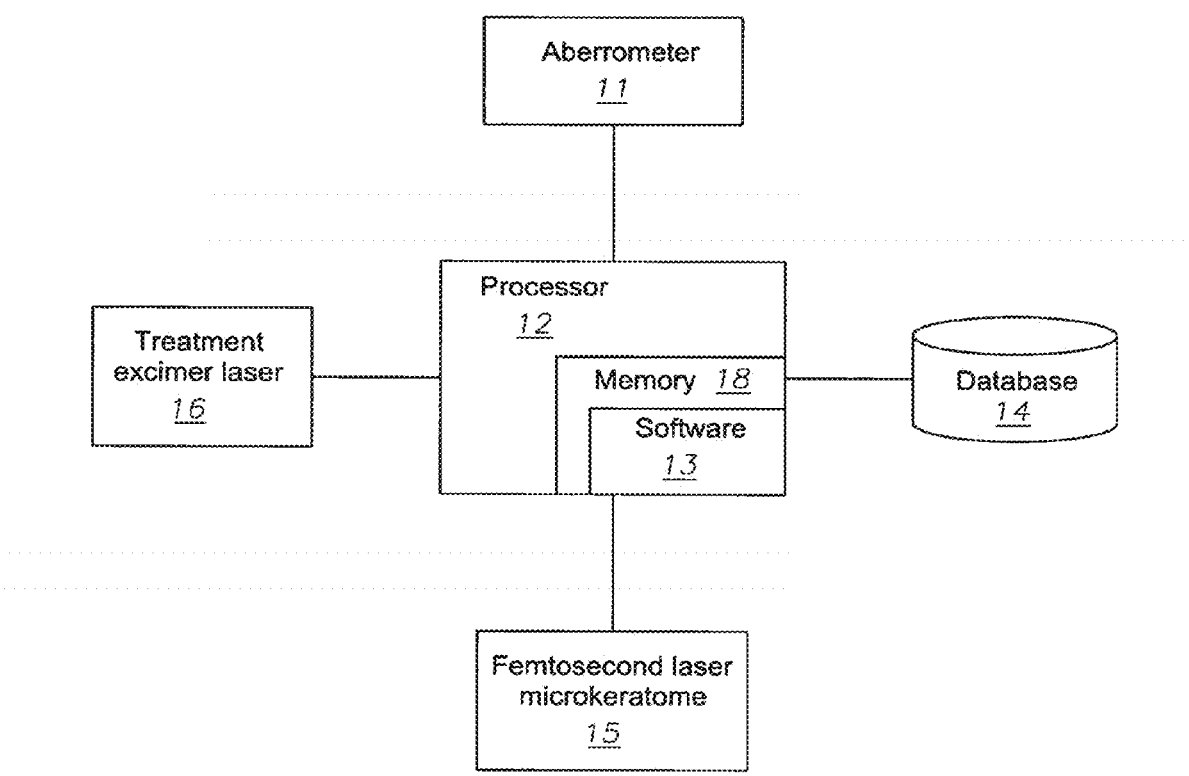
FIG. 1 is a schematic block diagram of a laser surgery system according to one embodiment of the present invention.

A description of the preferred embodiments of the present invention will now be presented with reference to FIGS. 1 and 2. An exemplary laser surgery system 10 is depicted schematically in FIG. 1, and an exemplary method 100, in FIG. 2.

The method 100 for performing wavefront-guided laser surgery on a cornea comprises the step of collecting anatomical information on an eye and wavefront data on a cornea using an aberrometer 11 (block 101). The collected anatomical information and wavefront data are transmitted to a processor 12 (block 102), which can comprise a memory 18 having a software package 13 installed thereon.

The-software package 13 includes code segments for calculating a corneal flap configuration, which can be an optimal corneal flap configuration, based upon the collected anatomical information and wavefront data (block 103). The optimal flap configuration-may include, for example, an optimal flap geometry. A database 14 is accessible by the processor 12, the database 14 containing data on previously performed corneal laser surgery (block 104). The data may include data from prior cases for trend analysis, and may include changes in wavefront profiles along actual flap geometry, so that any consistent effects of specific flap creations on aberration profiles can be factored into future treatments. An optimal ablation profile can thus be calculated using the collected anatomical information, the wavefront data, and the accessed data (block 105).

The processor 12 is further in controlling relation to a corneal flap-cutting device, for example, a femtosecond laser microkeratome 15. The femtosecond laser microkeratome 15, under control of the software package 13 stored in memory 18, is used to create a corneal flap based upon the calculated configuration (block 106). A reference mark may also be made on the corneal flap during the flap-cutting step for use in tracking a corneal position during laser surgery (block 107). The created configuration of the corneal flap is then measured (block 108), since the actual flap created may differ from the ideal target flap configuration in position and/or shape. These measured data are transmitted to the processor 12 (block 109).

The, using the anatomical information, the wavefront data, and the corneal flap measured configuration, a laser ablation pattern is calculated (block 110), and a treatment laser 16, for example, an excimer laser, is controlled by the processor 12 and software package 13 to create the calculated laser ablation pattern (block 111).

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A method for performing laser surgery comprising:
    measuring, by an aberrometer, a configuration of a corneal flap created by a femtosecond laser in a cornea of an eye;
    transmitting, by athe aberrometer, the measured configuration of the created corneal flap to a processor;
    calculating, by the processor, a laser ablation pattern for the eye using anatomical information of the eye and the measured configuration of the flap created in the cornea of the eye; and
    controlling, by the processor, a treatment laser to create the laser ablation pattern in the cornea.

2. The method of claim 1, further comprising collecting the anatomical information using an aberrometer.

3. The method of claim 1, the calculating the laser ablation pattern further comprising:
    calculating the laser ablation pattern using the anatomical information of the eye, the measured configuration, and wavefront data of the cornea.

4. The method of claim 3, further comprising calculating an ablation profile using the wavefront data of the cornea.

5. The method of claim 1, wherein the corneal flap configuration comprises a flap geometry.

6. The method of claim 1, further comprising making a reference mark on the corneal flap used to track a corneal position during the laser surgery.

* * * * *